US005551432A

United States Patent [19]

Iezzi

[11] Patent Number: 5,551,432

[45] Date of Patent: Sep. 3, 1996

[54] SCANNING CONTROL SYSTEM FOR ULTRASOUND BIOMICROSCOPY

[75] Inventor: Raymond Iezzi, Nassau County, N.Y.

[73] Assignee: New York Eye & Ear Infirmary, New York, N.Y.

[21] Appl. No.: 491,403

[22] Filed: Jun. 19, 1995

[51] Int. Cl.[6] .................... A61B 8/00

[52] U.S. Cl. .................... 128/660.09; 128/661.06; 128/662.03; 128/916

[58] Field of Search .................... 128/660.08, 660.09, 128/661.06, 662.03, 916; 73/620, 621

[56] References Cited

U.S. PATENT DOCUMENTS

| | | | |
|---|---|---|---|
| 4,841,978 | 6/1989 | Eventoff et al. | 128/660.09 |
| 4,870,970 | 10/1989 | Gray . | |
| 5,078,145 | 1/1992 | Furuhata | 128/916 |

*Primary Examiner*—George Manuel

*Attorney, Agent, or Firm*—Crummy, Del Deo, Dolan, Griffinger & Vecchione

[57] ABSTRACT

An ultrasonic probe which performs a two-dimensional scan is supported by a mount having a thread which is driven back and forth by a screw along a third axis. When a two-dimensional scan is completed in a first plane, a motor drives the mount along a guide to a second plane for the next scan. The separation between the planes being the same as the resolution in scanning within a plane. A housing having a slot with sidewalls is employed to guide the mount in traveling to successive plane locations along its axis. Means for orienting the housing in angular position and a support assembly provide moveable support to the orienting means so that minimal force is required to position the probe relative to the patient. An "auto-scroll" feature permits the operator to interactively pan through multiple, adjacent two-dimensional planes at programmable speeds and displacements along a third axis. A foot switch provides for hands-free bi-directional scrolling in a "user scroll" mode

21 Claims, 5 Drawing Sheets

211
210
17
10
20
16
40
51
30
18
36
50
60

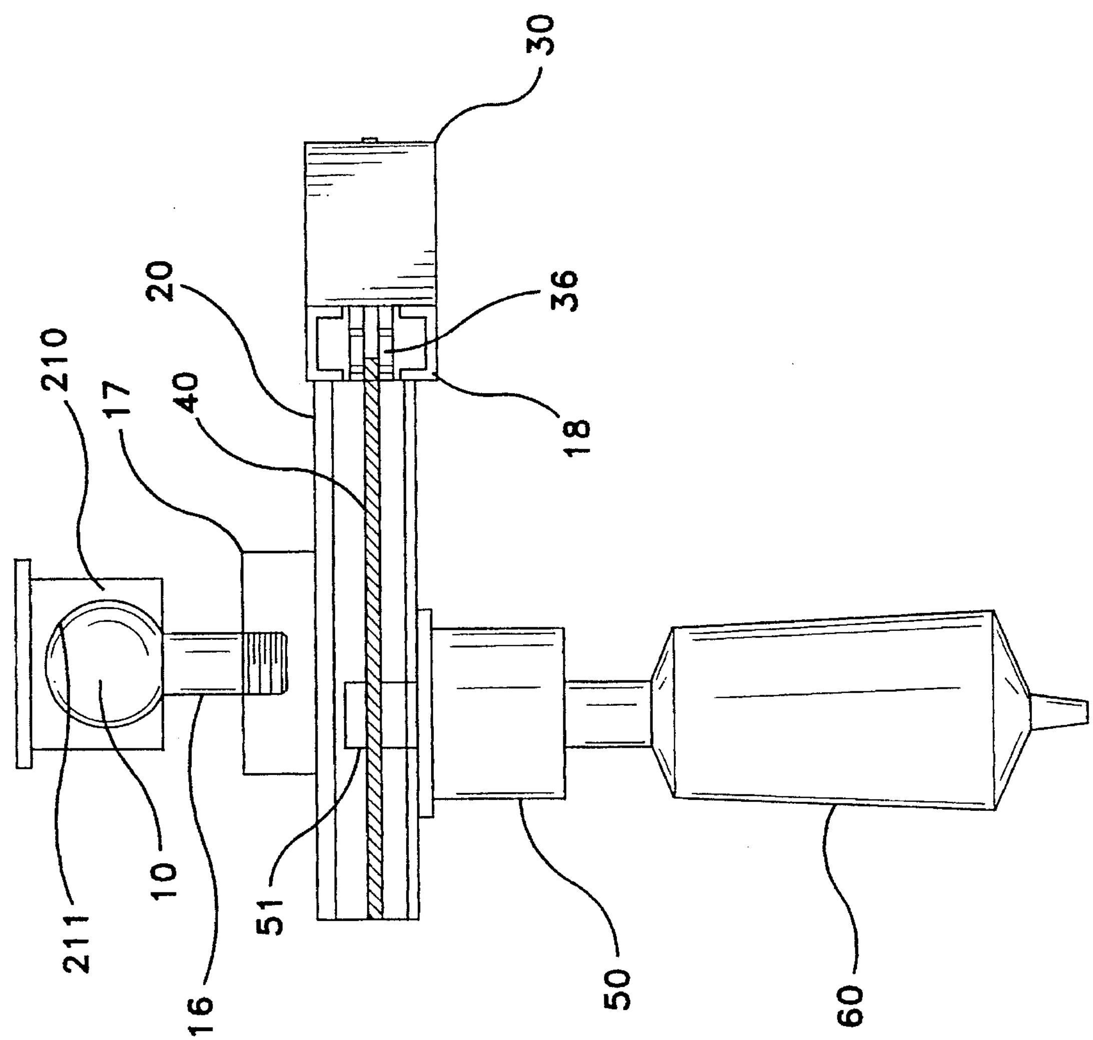
FIG—1

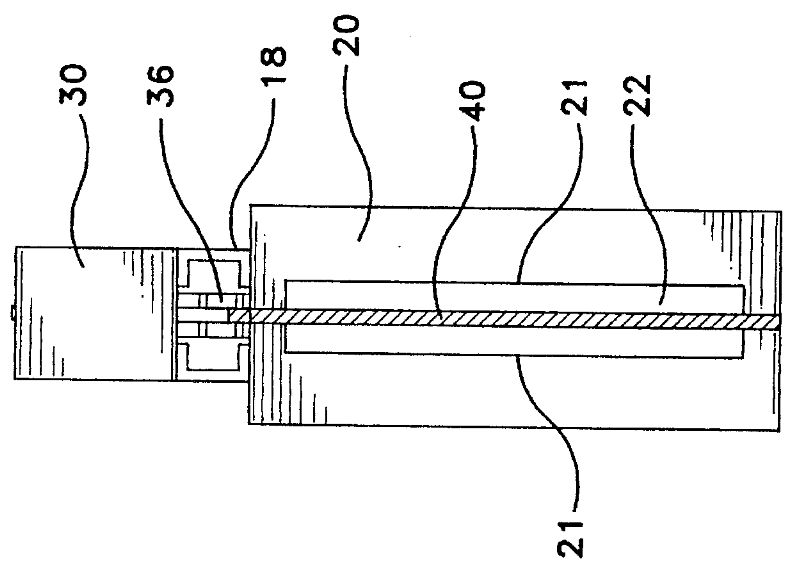
FIG—3
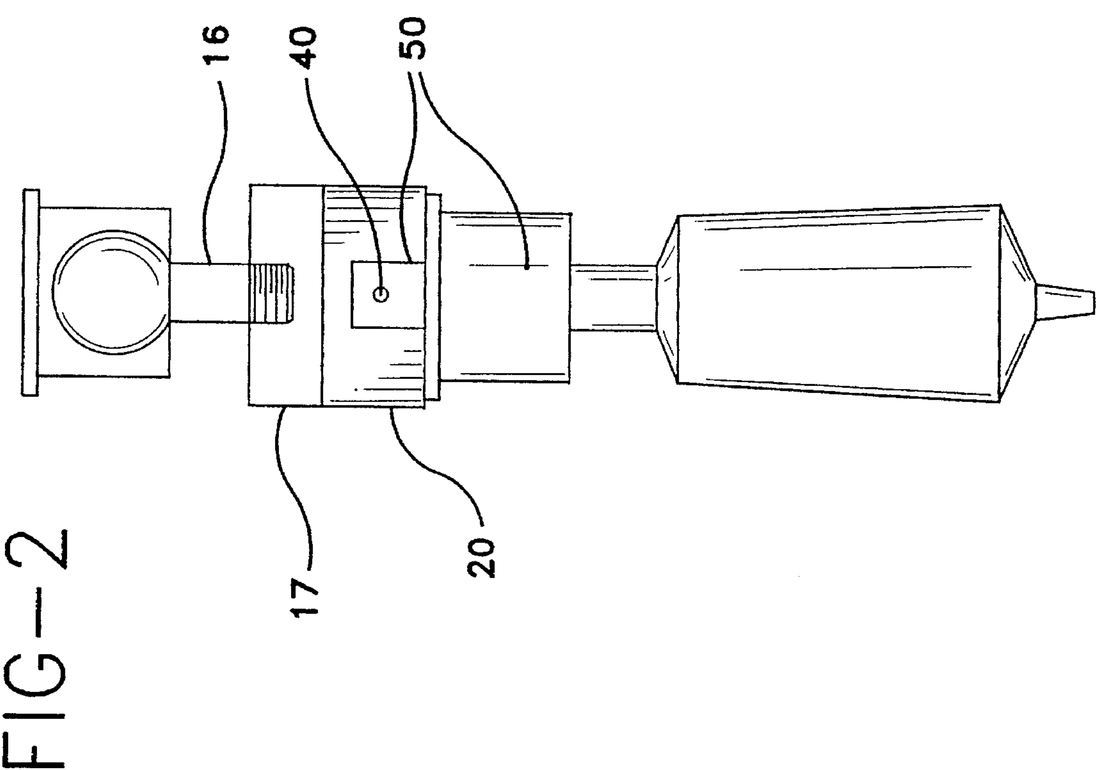
FIG—2

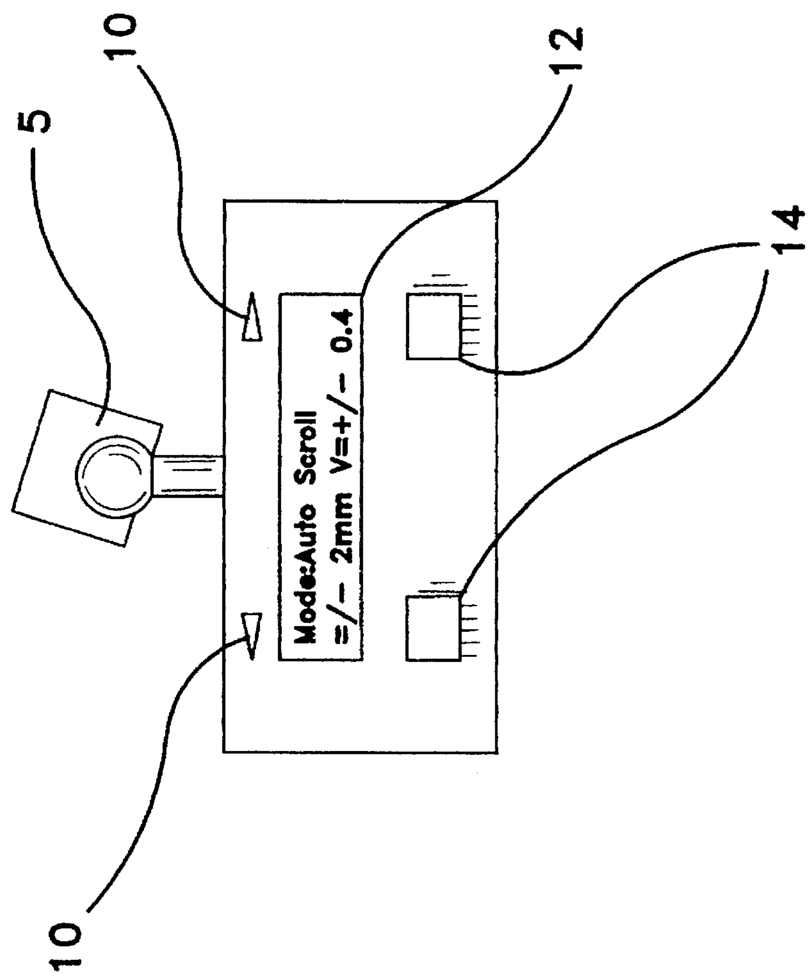
FIG—5B

SCANNING CONTROL SYSTEM FOR ULTRASOUND BIOMICROSCOPY

CROSS REFERENCE TO RELATED APPLICATION

This application is related to another U.S. Pat. application Ser. No. 08/492,229 entitled "Improved Imaging for Ultrasound Biomicroscopy" (Iezzi 2), with this application being concurrently filed with the present application, having the same inventor, and being incorporated herein by reference.

BACKGROUND OF THE INVENTION

1. Field of the Invention

This invention relates to ultrasound biomicroscopy, and in particular to the creation of three-dimensional images in real time of biological structures such as the eye.

2. Description of Related Art

The use of ultrasonic devices is proliferating in the medical arts to produce two-dimensional images of organ structures. An ultrasonic beam is pulsed, typically at 8 MHz, in successive directions in a plane and echo pulses from the tissue interfaces are detected, correlated in time and space, and constructed into a two-dimensional image.

To obtain greater resolution in the image, the frequency of the beam is being increased to the range of 50 to 100 MHz, which is particularly useful in the examination of the eye. These devices provide 50 micron resolution while scanning an area which is 5 millimeters square. This field of view is limited because higher frequency beams are attenuated more rapidly than lower frequency beams in the round trip path back to the detector. The transducer(s) providing and detecting the pulse is housed in a hand-held probe which is moved by the examining opthamologist approximately 3 millimeters from the surface of the cornea. An eye cup is placed around the eye and the volume between the cornea and the transducer is filled with a saline solution to couple the ultrasonic energy from the transducer into the eye. Scanning is performed with a real time image update rate of 8 frames per second. This modality has been useful in elucidating the anatomical correlates of a wide variety of disorders, including anterior segment tumors, plateau iris configuration, malignant glaucoma, and pigment dispersion syndrome. Ultrasound biomicroscopy has also been useful in the evaluation of intraocular lens haptic position, surgical complications, and intraocular foreign bodies. The ultrasound biological microscope is particularly useful where the optical examination is precluded by hyphema or corneal opacification.

Ultrasound biomicroscopic scans are two-dimensional planar images which are composed of discrete picture elements (pixels), defined by X and Y coordinates and a luminance value. Limitations in this art include the limited field of each image and the two-dimensional display. For example, where a foreign object enters the eye, the "track" of its entry is not well displayed by a two-dimensional representation. The high acoustic reflectance of foreign objects in the eye also makes visualization of their size, character, and extent more difficult.

A three-dimensional representation would provide information regarding spatial relationships between involved structures. These images are constructed from many two-dimensional images, stacked behind one another to provide an image with X, Y, and Z dimensions. They are composed of volumetric elements (voxels) which are defined by X, Y, and Z coordinates plus luminescence and transparency parameters. The transparency of a voxel describes the extent to which the observer is able to see through that part of the image to visualize underlying image information.

Accordingly, there is an increased need in the art for a clinically relevant, three-dimensional representation of the features of the eye with an increased field of view.

SUMMARY OF THE INVENTION

The present invention relates to three-dimensional ultrasound biomicroscopy, and in particular to the examination of the eye.

In one embodiment of the invention, an ultrasonic probe which performs a two-dimensional scan is supported by a mount having a thread which is driven back and forth by a screw along a third axis. When a two-dimensional scan is completed in a first plane, a motor drives the mount along a guide to a second plane for the next scan. The separation between the planes being the same as the resolution in scanning within a plane.

In another embodiment of the invention, a housing having a slot with sidewalls is employed to guide the mount in traveling to successive plane locations along its axis.

In a further embodiment, means for orienting the housing in angular position are added and a support assembly is added which provides moveable support to the orienting means so that minimal force is required to position the probe relative to the patient.

In each embodiment, the motor is bi-directional and it may be a constant speed motor or a stepper motor where the speed and stepping increment may be varied. The motor is controlled by a foot switch which permits the operator to scan in two directions without releasing the probe. A user terminal is adjustable for direct viewing by the operator and it indicates the mode of operation, the stepping increment, and the speed and direction of traverse of the probe. The screw, or transmission means, may be as conventional screw or a ball screw which minimizes backlash upon reversal of direction. The support means may be spring loaded or counter-balanced. An "auto-scroll" feature permits the operator to interactively pan through multiple, adjacent two-dimensional slices at programmable speeds and programmable distances of 2, 4, 5, or 14 millimeters along a third axis.

These and other features and advantages of the invention will be better understood with consideration of the following detailed description of the preferred embodiments taken in conjunction with the accompanying drawings.

BRIEF DESCRIPTION OF THE DRAWINGS

FIG. 1, is a partial sectional side view of one embodiment of the invention;

FIG. 2 is a side view of the embodiment shown in FIG. 1;

FIG. 3 is a bottom view of some elements in FIG. 1;

Figure 4:
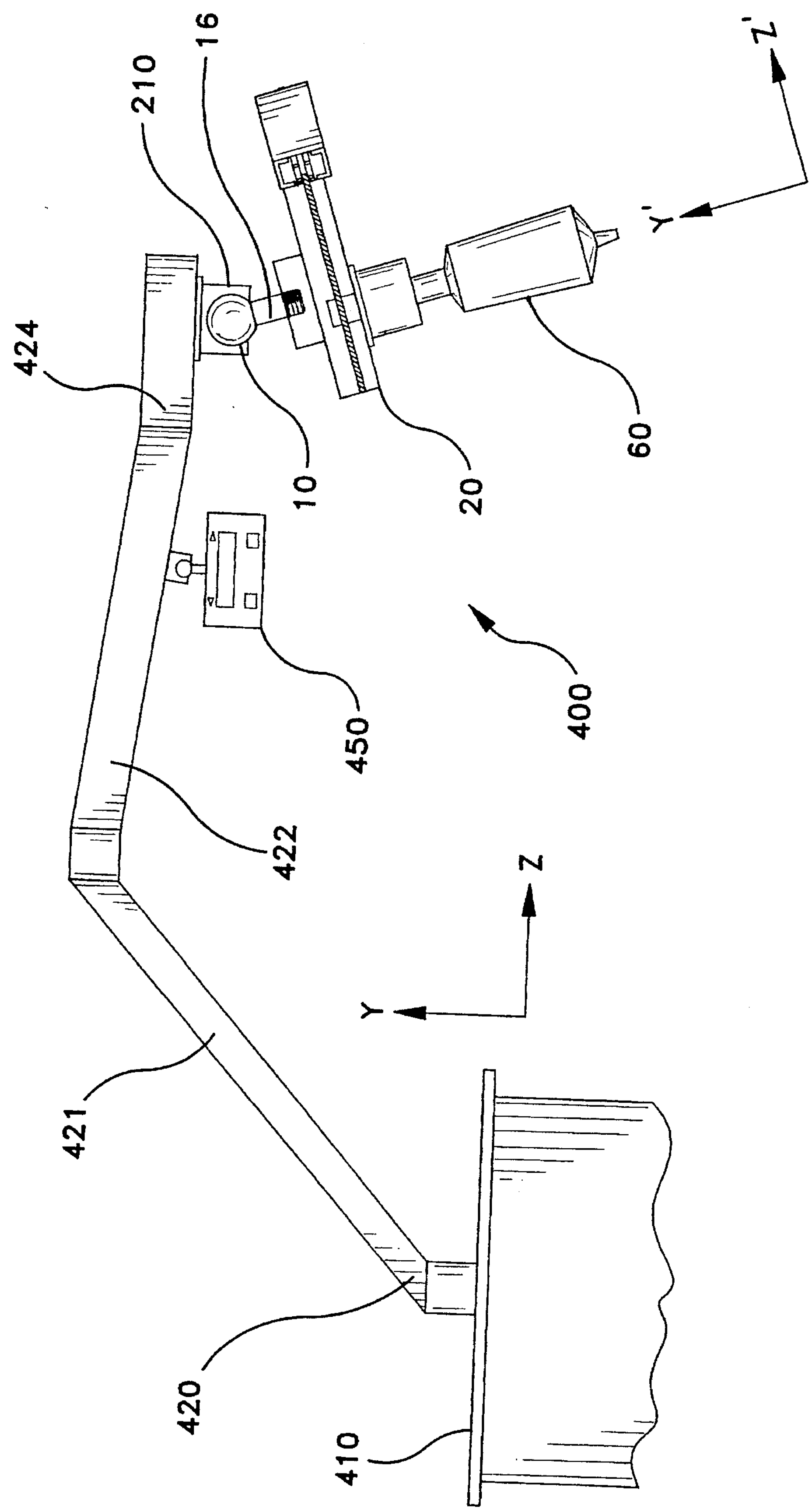
FIG. 4 is a side view of another embodiment of the invention.

The drawings are not to scale.

DETAILED DESCRIPTION OF THE PREFERRED EMBODIMENTS

Referring now to FIGS. 1, 2, and 3, there is shown apparatus 100 which is one embodiment of the invention wherein orienting means comprising a socket 210 having an inner surface 211 and a ball 10 which is in contact with and partially surrounded by inner surface 211. The ball supports extension 16. This arrangement allows the longitudinal axis of extension 16 to be oriented in space at any reasonable angle from a vertical, or Y, axis. Extension 16 can make an angle A with an X axis, coming out of the figure and normal to the Y axis, an angle B with the Y axis, and an angle C with a Z axis which goes left to right in the figure and which is normal to the other axes. Typical ball and socket configurations are well known and the angles A, B, and C can reach values of 60 degrees. A primed set of orthogonal axes will be used where extension 16 makes an angle with the examining room axes which are not equal to zero (See FIG. 4). The orienting means may also comprise a set of gimbals which are also well known.

Extension 16 screws into hub 17 which in turn supports housing 20 defining a slot 22 which has sidewalls 21 shown in FIG. 3. The sidewalls and the lower surface of the housing, used singly or in combination, comprise guide means for mounting means 50 which is adapted to slide along slot 22 of the housing. Mounting means 50 has an inner thread and is adapted to be driven along the slot in the Z' direction by transmission means 40 which has an external screw thread which mates with that of the mounting means and may be a conventional screw or a ball screw combination which is known in the art where preloading a threaded nut removes backlash when the direction of motion is reversed. Transmission means 40 is driven, in turn, by coupling means 36 which is adapted to transmit torque, absorb slight misalignment of axes, or even to change speed between driving and driven members. The coupling means is connected to motor 30 which may be a constant speed motor or a stepper motor whereby the speed and stepping increment may be varied. The motor is fastened to the housing by clamp 18. Mounting means 50 is shown in one configuration in FIG. 2 to penetrate through slot 22 to support probe 60. Various configurations of mounting means 50 cooperating with guide means are possible whereby mounting means 50 is driven in a controlled manner along a Z' axis while maintaining a spatial orientation in a plane normal to that axis. Probe 60 operates in that plane, here the X'–Y' plane, by sending pulses of ultrasonic energy in various directions within the X'–Y' plane and receiving echoes of these pulses which are converted into electrical signals by a transducer. When the scanning in a first plane is complete, motor 30 drives the transmission means to move mounting means 50 incrementally forward to a second X'–Y' plane where the scanning process is repeated. The scanning process is rapid compared to the rate of indexing, so that three-dimensional images have been assembled with a constant speed motor.

A foot switch and control electronics (not shown) provide for automatic or manual movement and speed control for the probe to scan bi-directionally in the Z direction. An operator may control the motor to "auto-scroll"—to interactively pan through multiple, adjacent scanning planes at programmable velocities along the Z' axis. The operator may also move the probe by means of a bi-directional foot switch for hands-free control in a "user scroll" mode. Depressing the left or right sides of the foot switch causes the motor to advance or return the probe at programmable velocities and displacements along the Z' axis.

In a preferred embodiment, probe 60 is part of an ultrasonic biomicroscope (UBM) system supplied by Humphrey Instruments, Inc., San Leandro, Calif., under the tradename UBM System 840. The probe operates at 50 MHz to provide a resolution in the Z-Y plane of 50 microns with a scan rate of 8 Hz. The transmission means has employed a 6-32 UNC thread which mates with the inner thread of the mounting means. The probe is advanced 50 microns in the Z' direction for each X'–Y' scan, to match the resolution in the planar scan. This is easily achieved with a stepper motor and has also been achieved with a constant speed motor at 15 rpm which advances the mounting means about 200 microns/sec. The length of scan in the Z direction is not limited, but a length of 15 millimeters has been useful in eye examinations which is a beneficial increase compared to the five millimeter field for the two-dimensional scan.

Referring now to FIG. 4, there is shown apparatus 400 which is a support assembly wherein arm mount 420 is attached to a stationary reference 410 such as a wall or a pedestal. The arm mount supports arms 421 and 422 which are spring loaded with variable tension to support socket connector 424 and socket 210 and its appended apparatus 100 which was previously described using the same reference numbers. Similar operation could be achieved with a counterbalanced arm to support apparatus 100, the point being that the person doing the scanning should need to exert only minimal force upon the probe and should be able to easily align the probe with six degrees of freedom; namely, X, Y, and Z rectangular coordinates of the examining room, and angles A, B, and C which relate the axes of the housing, X', Y', and Z', to the axes of the examining room User terminal 450 is also supported by arm 422.

Figure 5A:
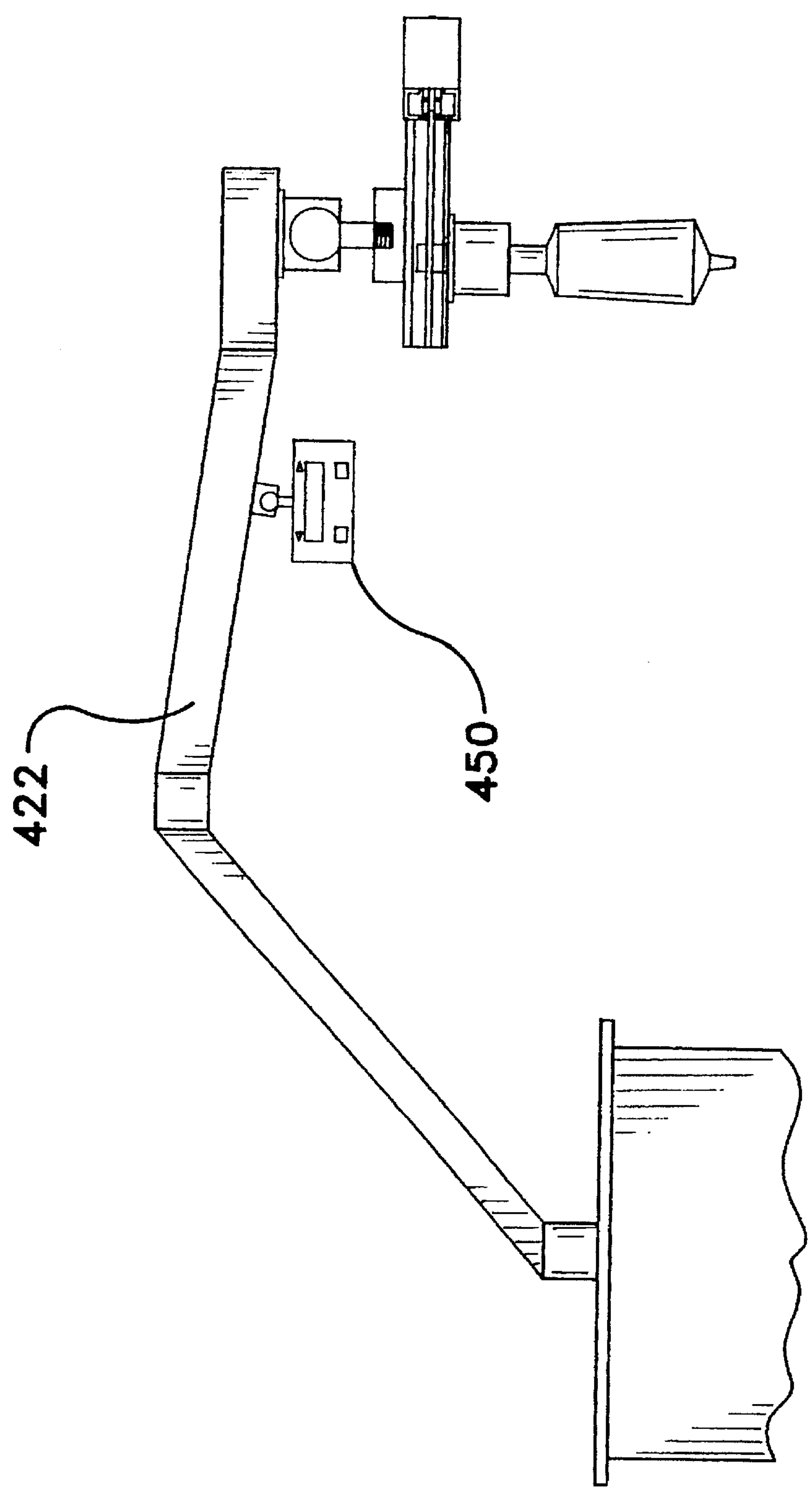
FIG. 5 is an enlargement of an element of the embodiment shown in FIG. 4.

Referring now to FIG. 5, there is shown an enlargement of user terminal 450. Socket 5 is attached to arm 422 and operates the same way and serves the same function as socket 210 of FIG. 1, namely, to provide three-dimensional angular orientation of the user terminal with respect to arm 422. The operator is thereby able to adjust the user terminal for direct viewing after the probe and arm 422 have been positioned over the patient. Indicators 10 are mounted to a control unit (not shown) and display the direction of probe motion along the Z' axis. Display 12 indicates the mode of scrolling; automatic or manual, together with the stepping increment and the speed of the probe. Selector buttons 14 provide input to the control system to change the mode of scrolling, the stepping increment, and the speed of the probe.

Apparatus 100 thus provides for the acquisition of multiple, sequential, parallel, aligned two-dimensional images which are reconstructed, as described in the related patent application, into a three-dimensional record which is capable of further manipulation and alternative presentations. The field of view is extended to 2.0 cm, which covers the anterior segment of the eye. In principle, it is possible to extend the field of view to any required distance. Thus, clinically relevant three-dimensional images are provided to the examining physician in real time permitting rescanning or scrolling through particular areas.

Changes and modifications in the specifically described embodiments can be carried out without departing from the scope of the invention. In particular, the mounting means may have a variety of shapes and may protrude or not from the housing. A variety of guide means may cooperate with the mounting means to provide sliding contact to the mounting means. The mounting means and transmission means may also be combined in a ball screw assembly.

I claim:

1. A scanning system for obtaining a three-dimensional image of an object by ultrasound biomicroscopy comprising:

a probe being adapted to transmit ultrasonic pulses of energy into a body in a series of directions, all lying in a scanning plane and being adapted to receive echoes of these pulses and to transform them into electrical signals;

means for mounting, having an inner thread, being connected to the probe;

means for guiding adapted to provide sliding contact to the mounting means;

means for transmission, having an external thread which is adapted to mate with the inner thread of the mounting means, being located on an axis which is normal to the scanning plane; and motor means having a shaft adapted to drive the transmission means in a bi-directional rotary motion thereby causing the probe to move between successive scanning planes.

2. The scanning system of claim 1 further comprising a housing having a surface adapted to support the motor means and the guiding means.

3. The scanning system of claim 2 wherein the housing defines a slot having two sidewalls being adapted to guide the mounting means.

4. The scanning system of claim 2 further comprising means for orienting the housing comprising:

an extension adapted to support the housing;

a ball connected to the extension; and a socket partially surrounding the ball;

wherein an inner surface of the socket contacts and supports an outer surface of the ball thereby providing three-dimensional rotational movement to the extension.

5. The scanning system of claim 4 further comprising a support assembly adapted to provide moveable support to the orienting means.

6. The scanning system of claim 1 further comprising means for coupling connected to and interspersed between the transmission means and the motor means.

7. The scanning system of claim 6 wherein the coupling means changes the rotational speed of the transmission means as compared to the rotational speed of the motor means.

8. The scanning system of claim 1 wherein the transmission means is a ball screw.

9. A scanning system for obtaining a three-dimensional image of an object by ultrasound biomicroscopy comprising:

a probe being adapted to transmit ultrasonic pulses of energy into a body in a series of directions, all lying in a scanning plane, and being adapted to receive echoes of these pulses and to transform them into electrical signals;

means for mounting, having an inner thread, being connected to the probe;

a housing defining a slot having two sidewalls being adapted to guide the mounting means and to provide sliding contact to the mounting means;

means for transmission, having an external thread which is adapted to mate with the inner thread of the mounting means, being located on an axis which is normal to the scanning plane;

motor means, mounted to the housing, having a shaft adapted to drive in a bi-directional rotary motion; and means for coupling connected to and interspersed between the transmission means and the motor means;

whereby the probe is moved between successive scanning planes.

10. The scanning system of claim 9 wherein the coupling means changes the rotational speed of the transmission means as compared to the rotational speed of the motor means.

11. The scanning system of claim 9 wherein the transmission means is a ball screw.

12. The scanning system of claim 9 wherein the motor means is a stepper motor.

13. The scanning system of claim 9 further comprising means for orienting the housing comprising:

an extension adapted to support the housing;

a ball connected to the extension; and a socket partially surrounding the ball;

wherein an inner surface of the socket contacts and supports an outer surface of the ball thereby providing three-dimensional rotational movement to the extension.

14. The scanning system of claim 9 further comprising a support assembly adapted to provide moveable support to the orienting means.

15. The scanning system of claim 9 further comprising a control system having a foot switch adapted to direct the operation of the motor means.

16. The scanning system of claim 15 further comprising a user terminal, connected to the control system, adapted to display operating parameters of the scanning system.

17. A scanning system for obtaining a three-dimensional image of an object by ultrasound biomicroscopy comprising:

a probe being adapted to transmit ultrasonic pulses of energy into a body in a series of directions, all lying in a scanning plane, and being adapted to receive echoes of these pulses and to transform them into electrical signals;

means for mounting, having an inner thread, being connected to the probe;

a housing, defining a slot having two sidewalls being adapted to guide the mounting means and to provide sliding contact to the mounting means;

means for transmission, having an external thread which is adapted to mate with the inner thread of the mounting means, being located on an axis which is normal to the scanning plane;

a bi-directional, variable increment stepper motor, mounted to the housing, having a shaft;

means for coupling connected to and interspersed between the transmission means and the motor shaft;

means for orienting the housing comprising an extension adapted to support the housing, a ball connected to the extension, and a socket partially surrounding the ball wherein an inner surface of the socket contacts and supports an outer surface of the ball thereby providing three-dimensional rotational movement to the extension; and a support assembly adapted to provide moveable support to the orienting means;

whereby the probe is positioned near an object and then moved between successive scanning planes.

18. The scanning system of claim 17 wherein the coupling means changes the rotational speed of the transmission means as compared to the rotational speed of the motor means.

19. The scanning system of claim 17 wherein the transmission means is a ball screw.

20. The scanning system of claim 17 further comprising a control system having a foot switch adapted to direct the operation of the motor means.

21. The scanning system of claim 20 further comprising a user terminal, connected to the control system, adapted to display operating parameters of the scanning system.

* * * * *